United States Patent [19]

Bosley

[11] Patent Number: 5,289,831
[45] Date of Patent: Mar. 1, 1994

[54] SURFACE-TREATED STENT, CATHETER, CANNULA, AND THE LIKE

[75] Inventor: Rodney W. Bosley, Bloomington, Ind.

[73] Assignee: Vance Products Incorporated, Spencer, Ind.

[21] Appl. No.: 871,644

[22] Filed: Apr. 21, 1992

Related U.S. Application Data

[63] Continuation-in-part of Ser. No. 823,323, Jan. 21, 1992, Pat. No. 5,201,314, which is a continuation-in-part of Ser. No. 383,174, Jul. 20, 1989, Pat. No. 5,081,997, which is a continuation-in-part of Ser. No. 320,967, Mar. 9, 1989, abandoned.

[51] Int. Cl.$^5$ ............................................. A61E 2/04
[52] U.S. Cl. ...................................... 128/899; 623/12
[58] Field of Search .................. 128/660.07, 662.02, 128/662.05, 654, 754, 899; 356/243; 623/12; 604/21; 204/168, 169

[56] References Cited

U.S. PATENT DOCUMENTS

| | | | |
|---|---|---|---|
| 3,605,750 | 9/1971 | Sheridan et al. | 604/21 |
| 4,111,190 | 9/1978 | Plumridge | 128/658 |
| 4,277,367 | 7/1981 | Madsen et al. | 436/8 |
| 4,322,164 | 3/1982 | Shaw et al. | 356/243 |
| 4,386,612 | 6/1983 | Roder et al. | 128/660.01 |
| 4,401,124 | 8/1983 | Guess et al. | 128/662.02 |
| 4,401,124 | 8/1983 | Guess et al. | 128/662.02 |
| 4,490,139 | 12/1984 | Huizenga et al. | 604/57 |
| 4,567,896 | 2/1986 | Barnea et al. | 128/660.07 |
| 4,582,061 | 4/1986 | Fry | 606/185 |
| 4,718,433 | 1/1988 | Feinstein | 128/662.02 |
| 4,718,907 | 1/1988 | Karwoski et al. | 623/12 |
| 4,743,493 | 5/1988 | Sioshansi et al. | 428/217 |
| 4,805,628 | 2/1989 | Fry et al. | 128/662.02 |
| 4,869,259 | 9/1989 | Elkins | 128/662.02 |
| 4,872,922 | 10/1989 | Bunker et al. | 148/4 |
| 4,911,172 | 3/1990 | Bui et al. | 128/662.06 |
| 4,968,006 | 11/1990 | Oliver | 266/78 |
| 5,048,530 | 9/1991 | Hurwitz | 128/662.05 |
| 5,081,997 | 1/1992 | Bosley, Jr. et al. | 128/662.05 |

FOREIGN PATENT DOCUMENTS

| | | | |
|---|---|---|---|
| 3501353 | 1/1984 | Fed. Rep. of Germany | 128/662.02 |
| 2272633 | 12/1975 | France | 128/662.02 |
| 8402838 | 8/1984 | World Int. Prop. O. | 128/662.02 |

OTHER PUBLICATIONS

Sommer, F. G., "A Phantom for Imaging Biological Fluids by Ultrasound and CT Scanning," *Ultrasound in Med. & Biol.*, vol. 6, pp. 135–140.

(List continued on next page.)

*Primary Examiner*—William E. Kamm
*Assistant Examiner*—George Manuel
*Attorney, Agent, or Firm*—Richard J. Godlewski

[57] ABSTRACT

Echogenic medical devices and methods of fabrication and of use are disclosed. The devices are adapted to be inserted into a patient. The device includes an elongated member including a material having an acoustic impedance different from that of the surrounding medium. The medium includes surrounding biological tissue or fluids surrounding the member when inserted into a passageway of the patient. The acoustic impedance of the elongated member is sufficiently different from the surrounding medium for enhancing an image produced in response to a sonic beam produced from imaging equipment. The elongated member also includes an interface layer of a high density metal of which the deposition on the base material of the member is ion beam assisted. The interface layer includes an outside surface having a plurality of particulate-type, discontinuous curved surfaces of partially spherical indentations formed therein or spheres extending therefrom. The difference between the acoustic impedances of the interface layer and the surrounding medium along with the discontinuous surfaces of the interface layer cooperate in response to a beam from sonic imaging equipment to significantly enhance the image of the medical device member.

19 Claims, 11 Drawing Sheets

OTHER PUBLICATIONS

Madsen, E. L., et al., "An anthropomorphic torso section phantom for ultrasound imaging," *Med. Phys.*, vol. 7, Issue 1, pp. 43-50.

Sioshansi, Piran, Ph.D., "Surface Engineering by Ion Implantation," *Precision Metal*, Dec. 1988, vol. 46, No. 12, pp. 15-19.

Baier, R. E., "Selected Methods of Investigation for Blood-Contact Surfaces," *Annals New York Academy of Sciences*, Dec. 28, 1987, vol. 516, pp. 68-77.

Rittle, K. H. et al., "*Escherichia Coli* Retention on Solid Surfaces as Functions of Substratum Surface Energy and Cell Growth Phase", *Biofouling*, 1990, vol. 2, pp. 121-130.

Baier, R. E., "Conditioning Surfaces to Suit the Biomedical Environment: Recent Progress," *Journal of Biomechanical Engineering*, Nov. 1982, vol. 104, pp. 257-271.

Glantz, Per-Olof J. et al., "Comparative Clinical Wettability of Teeth and Intraoral Mucosa", *J. Adhesion Sci. Technol.*, 1991, vol. 5, No. 5, pp. 401-408.

Baier, R. E. et al., "Adhesion: Mechanisms That Assist or Impede It," *Science*, 1968, vol. 162, pp. 1360-1368.

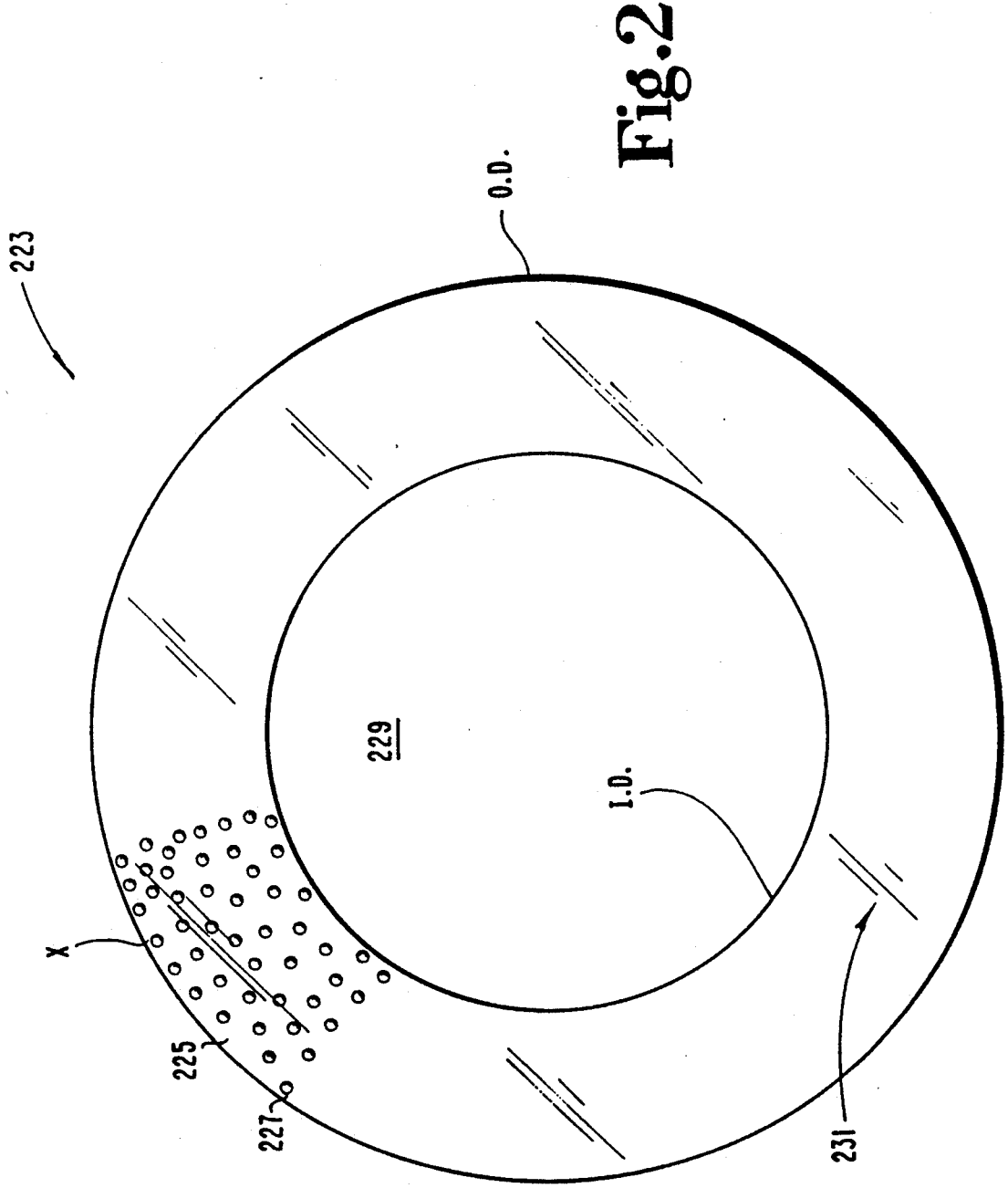

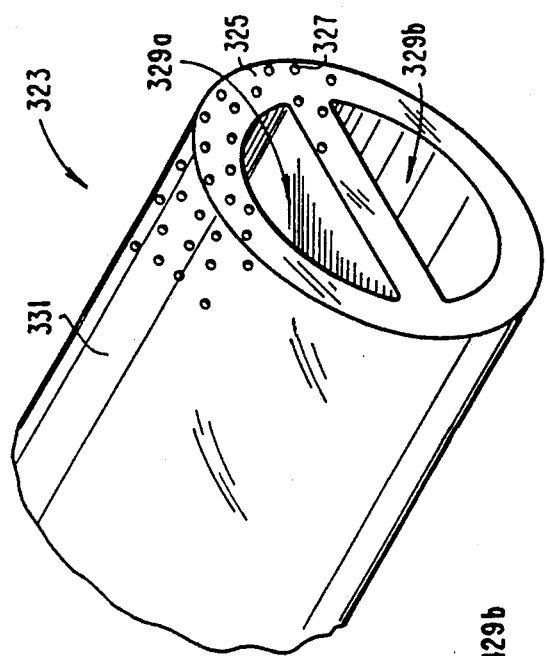
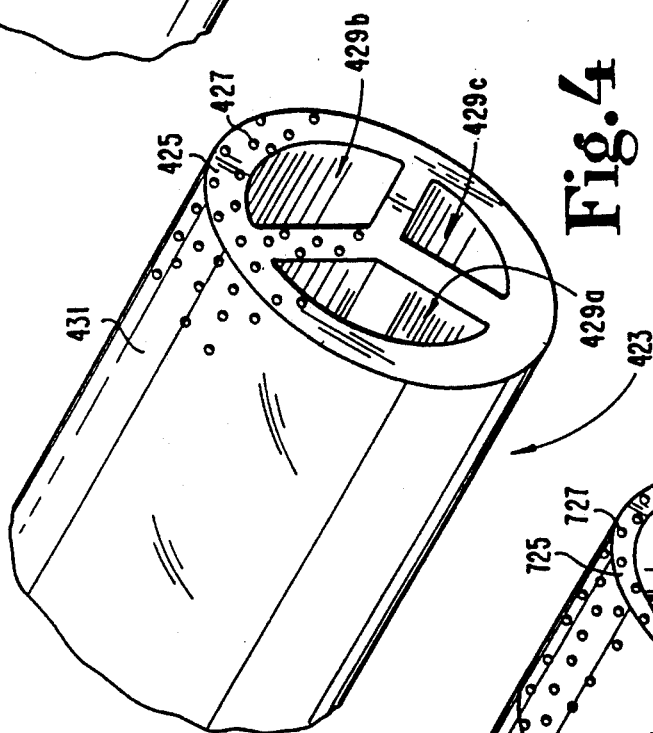
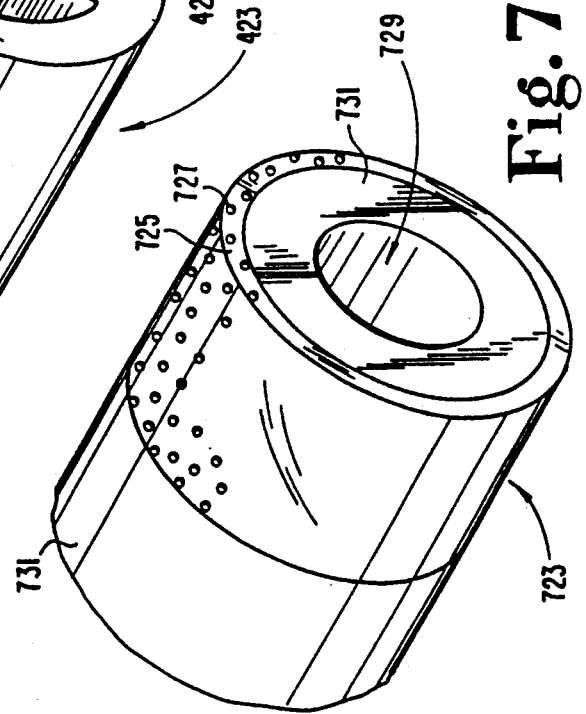

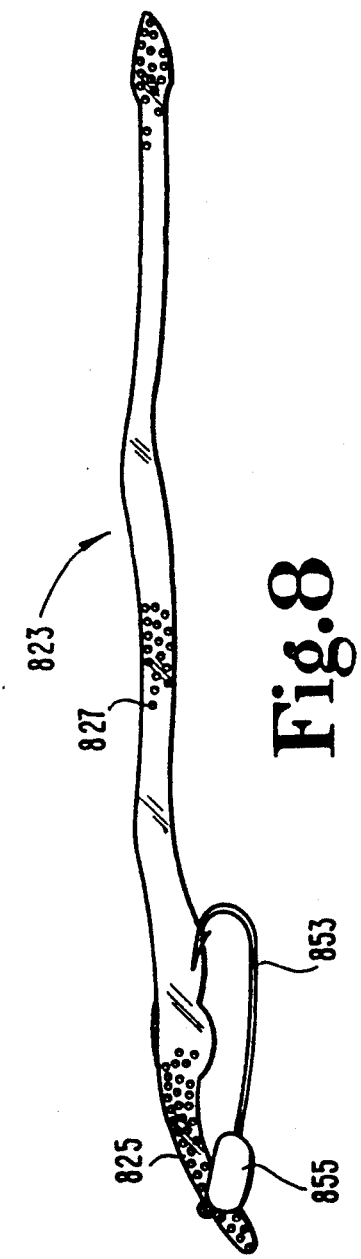

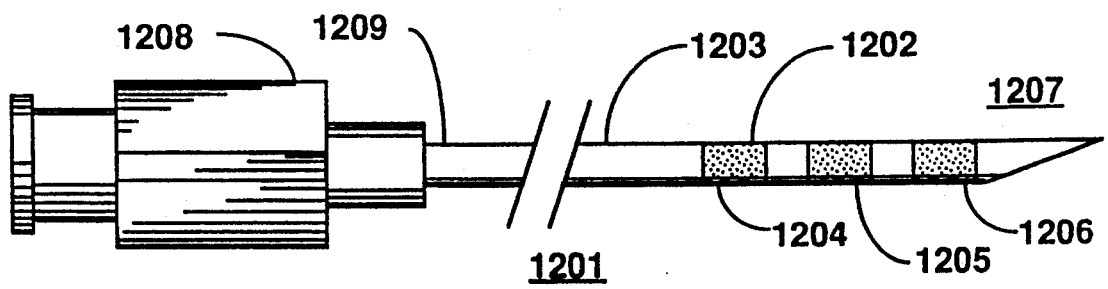
Fig. 12
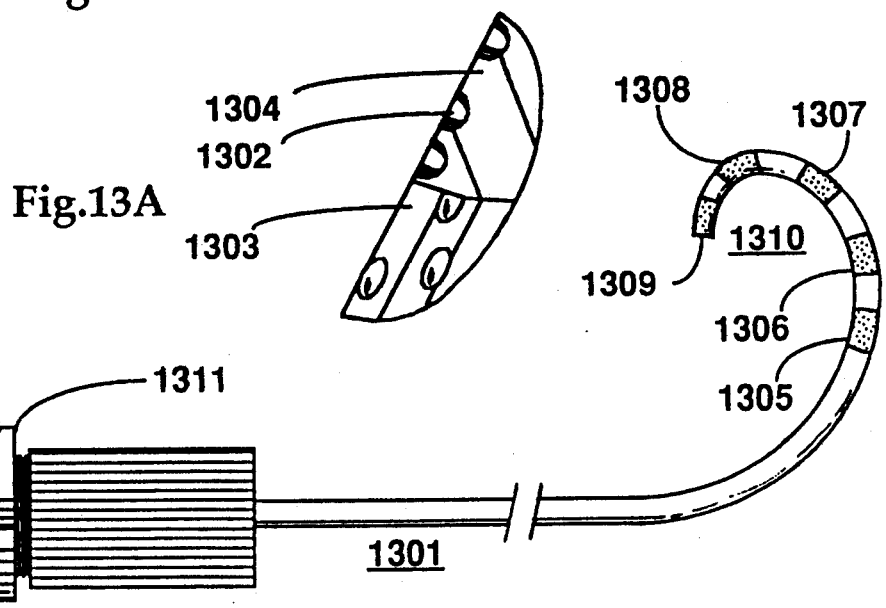
Fig. 13A
Fig. 13
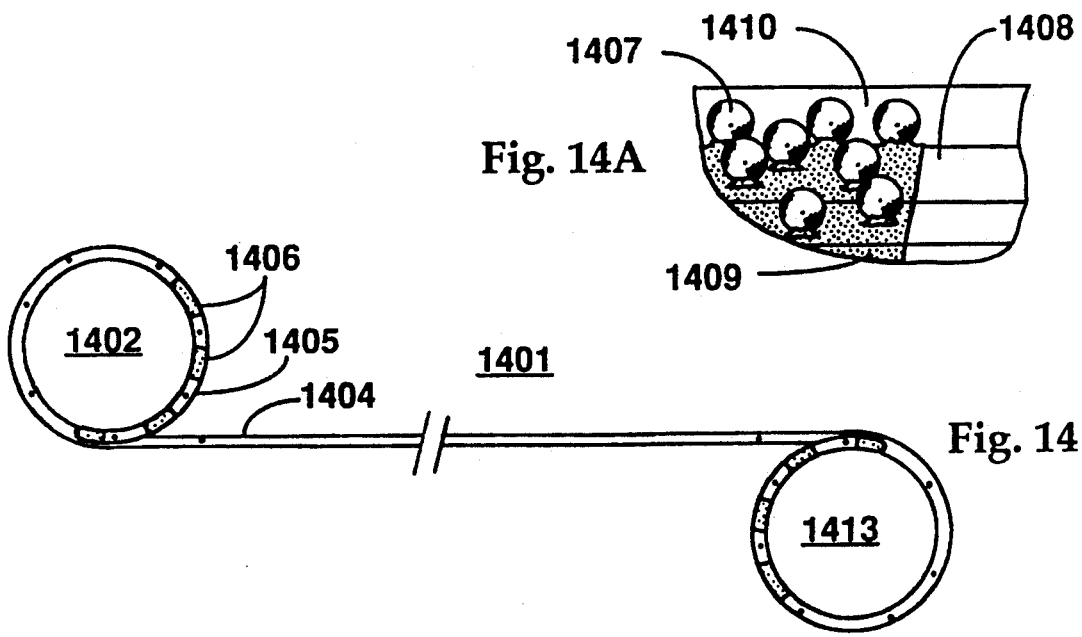
Fig. 14A
Fig. 14

SURFACE-TREATED STENT, CATHETER, CANNULA, AND THE LIKE

CROSS-REFERENCE TO RELATED APPLICATIONS

This application is a continuation-in-part of application Ser. No. 07/823,323, filed Jan. 21, 1992, entitled "Echogenic Devices, Material and Method", now U.S. Pat. No. 5,201,314 which is a continuation-in-part of application Ser. No. 07/383,174, filed Jul. 20, 1989, entitled "Echogenic Devices, Material and Method", now U.S. Pat. No. 5,081,997, which is a continuation-in-part of application Ser. No. 07/320,967, filed Mar. 9, 1989, entitled "Echogenic Devices, Material and Methods", now abandoned. This application is also related to application Ser. No. 07/871,645, entitled "Treated Surface Catheter for Extracorporeal Treatment", and filed concurrently herewith.

TECHNICAL FIELD

This invention relates generally to medical devices such as stents, catheters, cannulae, and the like and particularly to surface-treated stents, catheters, cannulae, and the like, which have a surface that is resistant to the formation of thrombus, fungus, bacteria, and encrustations thereon.

BACKGROUND OF THE INVENTION

Ultrasonic imaging in the medical field is widely used for a variety of applications. In addition to imaging physiological structures and tissue such as organs, tumors, vessels, and the like, it is often desirable for a physician or technician to have an image of a medical device which has been inserted into the tissue or passageway of a patient. The types of devices which are surgically sterilized and inserted into patients are many. Typical examples include: needles, catheters and a variety of other medical products such as stents, dilators, pacing leads, introducers, angiography devices, angioplasty devices, pacemakers, inpatient appliances such as pumps and other devices. Various approaches have been used to enhance ultrasonic imaging by modifying the reflective surface characteristics of these devices.

U.S. Pat. No. 4,401,124 to Guess et al. discloses a system for reflection enhancement of a biopsy needle showing grooves cut in the tip of the needle. The reflection coefficient of the needle is enhanced by the use of a defraction grading disposed on the surface of the needle. The defraction grading is formed by the substantially parallel grooves, where the distance between the depth of adjacent grooves is a function of the wavelength of the ultrasound imaging system and the angle of the incident beam with respect to the surface of the needle. The spaced grooves provide constructive interference of the beam, thereby yielding maximum reflection back along the line of the incident beam.

Although the Guess et al. system with its helical defraction grading around the tip of the needle, along with other needles having similar rings, may provide some degree of signal reinforcement along the axis of incident energy, the overall image is far from ideal. Further, needles of this type typically exhibit a marked loss of resolution as the needle is oriented away from an optimum angle relative to the incident ultrasound beam, which angle depends upon the particular ring parameters.

What is needed is a device which provides more accurate monitoring of a surgical instrument such as a needle inserted into the body, which does not require a specific angle of orientation for its efficiency, and which is inexpensive to manufacture.

Another system for enhancing the ultrasound image of a portion of a medical instrument is disclosed in U.S. patent application, Ser. No. 194,861, filed May 17, 1988, and owned by the assignee of the present application.

Furthermore, medical devices exist in which radiopaque stripes or additives are utilized to make the medical device appear on an X-ray machine or other radiographic device. For example, U.S. Pat. No. 365,750 to Sheridan et al. discloses an X-ray type catheter having an X-ray opaque pigment on the catheter tube.

One disadvantage of some X-ray opaque medical devices is that there is a risk of the X-ray opaque material flaking or peeling off and remaining in the patient. Furthermore, with these X-ray opaque paints and with the outer surface treatment utilized in the ultrasonic imaging device, fabrication expenses are increased.

Another problem with catheters, stents, cannulae, and the like that are used for extracorporeal or indwelling treatment is the formation of thrombus, bacteria, fungus, and mineral encrustations when positioned in a vessel or duct for an extended period of time. This is commonly due to the rough surface of the device of which thrombus and the like readily attach thereto. In addition, the rough surface of the catheter and the like often exhibits a high coefficient of friction, which makes it difficult for inserting the device into the vessel or duct through, for example, an introducer sheath.

SUMMARY OF THE INVENTION

The foregoing problems are solved and a technical advance is achieved with an illustrative echogenic medical device that is insertable into a medium such as the tissue or a passageway of a patient and imageable with sonic imaging equipment. The illustrative device includes an elongated member for insertion into a surrounding medium such as the biological tissue or passageway of a patient. The member includes a material having an acoustic impedance different from the acoustic impedance of the surrounding medium. The difference between acoustic impedances of the member material and the surrounding medium enhances an image produced in response to a sonic beam from the imaging equipment. The elongated member also includes an interface having a shape that is responsive to the sonic beam for producing the image.

As a departure in the art, the shape of the interface has been formed with a dimension that is less than a wavelength of the incident sonic beam. Furthermore, the shape advantageously includes a dimension such as a radius of curvature which is much less than the wavelength of the sonic beam. In one embodiment of the device, the interface includes the outside surface of the elongated member material. In the surface is a plurality of partially spherical indentations for producing a scattered component of the image in response to the incident beam. This image is produced regardless of the incident beam angle of which prior art devices depend for producing a reflected or constructive interference image. Advantageously, the scattered component of the image is produced when the radius of the partially spherical indentations or a dimension of another geometric shape or surface are much less than the wavelength of the incoming sonic beam. The difference in the acoustic impedances of the member material and the surrounding medium enhances the intensity of the scattered component of the image.

In another illustrative embodiment of the device, the elongated member includes a substance such as a plurality of spherically or other geometrically-shaped particles that have a predetermined contour for establishing the interface. This contoured substance is contained within the material of the elongated member or alternatively or in combination attached to or embedded in the outside surface of the member material. In one case, the member material comprises a plastic for surrounding spherically-shaped glass particles. In another case, the glass particles are attached to the outside surface of the member with an adhesive material. In still another case, the particles are embedded in the outside surface of the member material. In still another illustrative embodiment, the contoured substance such as the glass particles are affixed to the outside surface of a stainless steel member using, for example, another material such as silver solder. In such instance, the substance has an acoustic impedance different from at least one of the impedances of the member material and surrounding tissue for enhancing the image produced in response to the sonic beam. The silver solder also presents another acoustic impedance to enhance an image.

In yet another illustrative embodiment of the device, the member includes a base material such as a flexible polyurethane material with an interface layer deposited thereon for further enhancing the image produced in response to the sonic beam. The interface layer comprises a material different from the base material and has an acoustic impedance different from the acoustic impedance of the medium. The acoustic impedance of the deposited interface layer material is advantageously much higher than that of the base material or surrounding medium. As a result, the difference between the acoustic impedances of the interface layer and the medium is advantageously increased for further enhancing the image of the member. As previously described, the interface layer has a particulate-type, discontinuous curved surface or contour with a dimension less than a wavelength of a sonic beam from the imaging equipment. The increased difference between these acoustic impedances and the curved surface or contour cooperate in response to a sonic beam from the imaging equipment to produce a significantly enhanced image of the member.

The base material of the device includes a deposition surface. The member also includes a particulate in the deposition surface for forming the particulate-type discontinuous surface or contour in the deposition surface. In one aspect, the particulate includes a plurality of particles having at least a partially spherical shape. The particles comprise a high density metal such as barium or tungsten or a glass material of a generally spherical shape. The base material of the member comprises a matrix material for fixedly positioning the particles in the deposition surface. In another aspect, the particulate-type discontinuous curved surface includes a plurality of at least partially spherical indentations in the deposition surface of the base material. The indentations or particles advantageously include a radius in the range of 0.5 to 50 microns. The interface layer material is deposited over the at least partially spherical particles or indentations to advantageously further enhance the image of the device in response to a sonic beam from the imaging equipment.

The deposition of the interface layer material on the deposition surface of the member base material is ion beam assisted. The interface layer material advantageously includes a metal from a group consisting of titanium, tungsten, barium, bismuth, platinum, silver, gold, and palladium. The base material of the member advantageously comprises a flexible material from a group consisting of polyurethane, polyethylene, polyvinyl chloride, polypropylene, polyester, and silicone. The base material group also comprises a flexible C-FLEX TM material, which is also advantageously used in medical devices such as catheters and stents. To advantageously maintain the inherent flexibility of the medical device such as a catheter or stent, the deposited interface layer is extremely thin and has a thickness in the range of 2,000 to 3,200 angstroms. For rigid medical device applications, the base material comprises a metal such as stainless steel on which the high density metal interface layer is deposited thereon.

The present invention also includes a method for sonically imaging an echogenic medical device in biological tissue. The method includes selecting a device having an acoustic impedance different from the acoustic impedance of the biological tissue. A difference between the impedances of the device and tissue enhances the image produced in response to a sonic beam from sonic imaging equipment. The method further includes inserting into the tissue an elongated member of the device including an interface having a shape responsive to the sonic beam for producing the image. As previously suggested, the shape includes a plurality of at least partially spherical indentations having a dimension less than a wavelength of the sonic beam. In particular, the radius of the indentations is much less than the wavelength of the sonic beam for producing a scattered component of the image. Also included in the method is directing a sonic beam toward the elongated member when inserted in the tissue and receiving the image produced from the interface in response to he sonic beam.

Another method of the present invention includes manufacturing the echogenic medical device for insertion into biological tissue and imageable with sonic imaging equipment. The illustrative manufacturing method includes forming an elongated member of the device from a material such as stainless steel or plastic having a predetermined acoustic impedance different from the acoustic impedance of the biological tissue. The difference between the acoustic impedance of the elongated member material and the biological tissue enhances an image produced in response to a sonic beam from the imaging equipment. Advantageously, the greater the difference between the member material and the biological tissue, the greater the enhancement of the image produced. The method also includes forming an interface in the member for producing the image in response to the beam. The interface, again having a shape with a dimension less than a wavelength of the sonic beam. In one embodiment, the outside surface of the elongated member material is indented with partially-spherical projections for producing a plurality of at least partially spherical indentations. In another embodiment, the method includes forming the interface by attaching a plurality of at least partially spherical particles to the surface of the elongated member. The particles having an acoustic impedance having at least said predetermined difference between at least one of the two impedances of the elongated member and biological tissue. A preferred diameter for the partially-spherical indentations is in the range of between 1 to 100 microns.

In another aspect of the invention, the echogenic device comprises an elongated body member including a composite material echogenically imageable. The composite material includes a formable matrix material with discrete sound reflective particles made from a material different from and more sonically reflective than the matrix material being embedded in the matrix material and the surface thereof to enhance the echogenicity of the body member. An interface layer is also advantageously deposited on the surface of the matrix to further enhance the image produced in response to a beam from sonic imaging equipment. Accordingly, the present invention provides a superior product which is readily manufactured and is reliable in use. Furthermore, the present invention may easily be made biological inert and sterile for patient safety.

Although the present invention has many applications, it is particularly envisioned to be useful in medical devices such as catheters, stents, and other products which are inserted into the tissue or passageway of a patient. These advantages are provided by forming the device, such as a catheter, from a composite material which includes a formable matrix material having discrete sound reflective particles embedded therein. In the preferred embodiment, the matrix material consists of polyethylene. The discrete sound reflective particles embedded therein are preferably glass microspheres having a diameter of about 5 microns. This composite material still maintains the requisite flexibility for many medical applications, while providing echogenicity throughout the body of the device. In this way, the physician may observe a full image of the medical device in the patient.

Furthermore, these advantages may be combined by including in the composite material a radiopaque material such as barium or tungsten to provide imaging with radiographic equipment. These advantages may be incorporated without a significant modification to the fabrication technique presently being used. The reflective particles, and optionally the radiopaque material, are mixed into the matrix material prior to forming the device by, for example, extrusion in the case of most catheters. Thus, no additional post extrusion fabrication steps are required to provide the desired echogenicity and a high level of quality control may be maintained.

Another aspect of the present invention includes a method of sonically imaging the device. This method includes providing an echogenic body member including composite material echogenically imageable, the composite material including a formable matrix material with discrete sound reflective particles made from a material different than and more sonically reflective than a matrix material being embedded in the matrix material to enhance the echogenicity of the body member; positioning the echogenic body member in a sonic imaging beam; and generating an image of the echogenic body member including the sound reflective particles from the sonic imaging beam.

The foregoing problems are solved and a technical advance is achieved with an illustrative catheter, stent, cannulae, and the like having a treated outer surface that is, for example, bombarded in a vacuum chamber environment with ions such as argon, nitrogen, and the like. This bombardment or treatment process smoothens the outer surface of the catheter, stent, cannulae, and the like, thereby reducing the coefficient of friction of the outer surface and making the outer surface resistant to the formation of thrombus, fungus, bacteria, and encrustations thereon.

One object of the present invention is to provide an improved echogenic device and materials.

Another object of the present invention is to provide an improved method of fabricating and of using echogenic devices.

Another object of the present invention is to provide improved catheters, dilators, stents, pacing leads and other appliances to be surgically inserted into medical patients.

Another object of the present invention is to provide a device, and a method of fabricating a device, which is both sound reflective and radiopaque for use with either ultrasonic equipment or with radiographic equipment.

These and other objects and advantages of the present invention will be apparent from the specification and the drawings.

BRIEF DESCRIPTION OF THE DRAWINGS

FIG. 2 is a cross-sectional view of a second embodiment of the present invention;

FIG. 3 is a cross-sectional perspective view of a third embodiment of the present invention;

FIG. 4 is a cross-sectional perspective view of a fourth embodiment of the present invention;

FIG. 7 is a cross-sectional perspective view of a fifth embodiment of the present invention;

FIG. 8 is a side elevational view of a sixth embodiment of the present invention;

FIG. 12 is a partial view of a needle embodiment of the present invention;

FIG. 13 is a partial view of a catheter embodiment of the present invention;

FIG. 13A is an enlarged portion of the medical device of FIG. 13;

FIG. 14 is a partial view of a stent embodiment of the present invention;

FIG. 14A is an enlarged portion of the medical device of FIG. 14;

DETAILED DESCRIPTION

Figure 1:
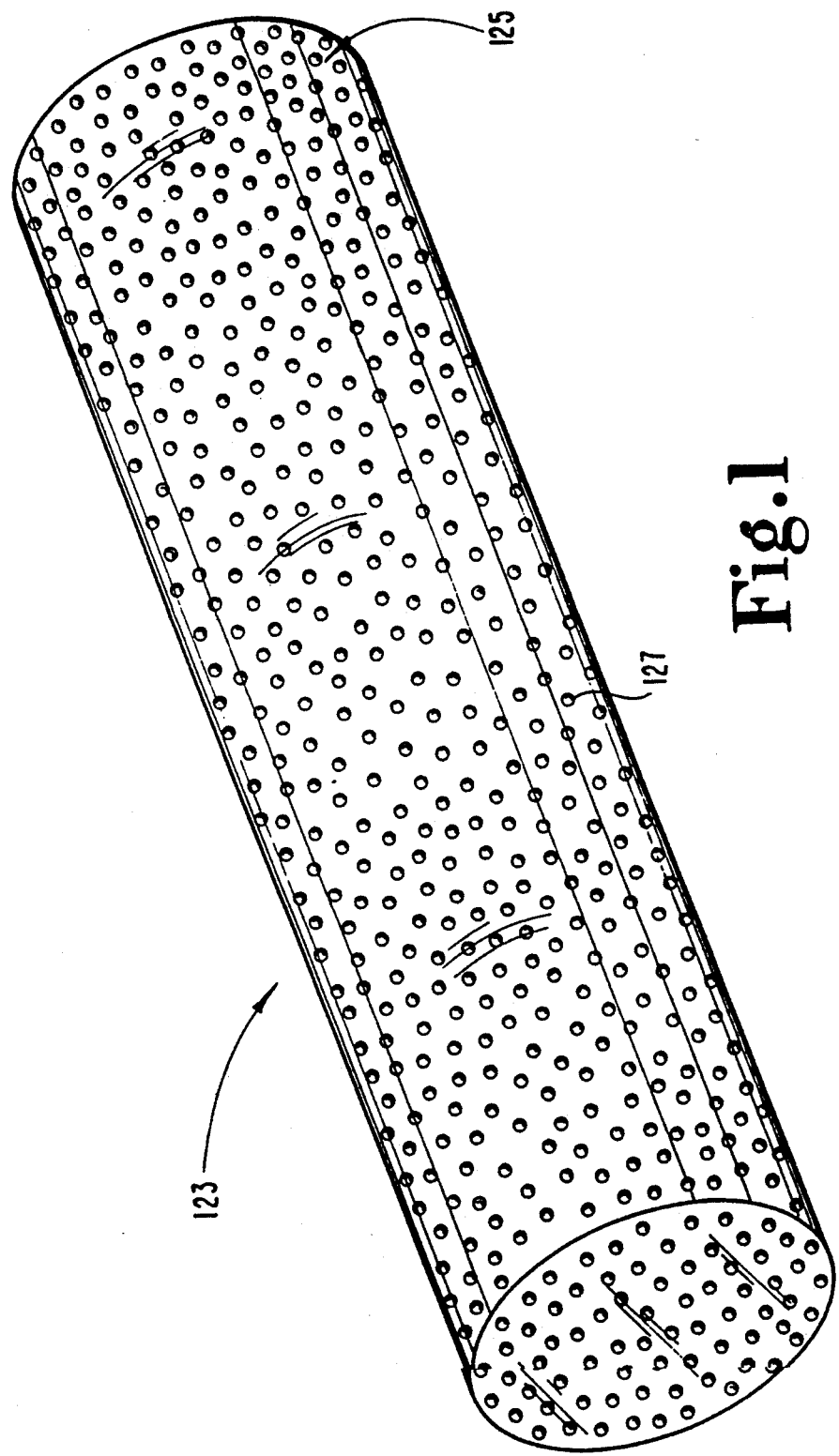
FIG. 1 is a perspective view of a first embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device and method, and such further applications of the principles of the invention as illustrated therein being contemplated as would normally occur to one skilled in the art to which the invention relates.

Referring to FIGS. 1–18, various embodiments of the present invention are illustrated, each embodiment having a different number in the hundreds digit. Accordingly, there is a "100" series, a "200" series, ..., a "1500" series, and a "1700" series.

Referring to FIG. 1, a first embodiment of the present invention is shown. Echogenic body member 123 is a part of an echogenic device to be sonically imaged. The present invention may be utilized in a multitude of devices including medical devices, the following being only a set of possible examples: catheters, devices made from catheters, stents, pacing leads, introducers, pacemakers, ultrasonic rulers, in-patient appliances such as pumps, balloons, dilators, endoscopes, sphincterotomes, angiographic equipment, surgical implants, and other such devices. Echogenic body member 123 is at least partially made up of a composite material which is echogenically imageable in the patient, such as by the use of ultrasonic imaging equipment. The composite material includes matrix material 125 with discrete sound reflective particles 127 embedded in matrix material 125. Preferably, matrix material 125 is a plastic. Examples of suitable plastics may include urethane, ethylene, silicone, polyethylene, polyurethane, polyvinyl chloride, polypropylene, polyester, and polytetrafluorethylene. Preferably, matrix 125 is a formable, pliable material which may be molded and/or extruded to a variety of shapes, depending upon a specific application.

The sound reflective particles 127 are embedded in matrix material 125. Particles 127 are preferably made of a hard material, and it has been found that small glass particles are especially well suited for this application. Specifically, glass particles having a generally spherical shape forming glass microspheres are very suitable. Glass microspheres with an outer diameter of about 5 microns is one acceptable size. Other sized particles may be utilized as, for example, ranging between 1 and 50 microns and beyond. Furthermore, the particles do not necessarily have to be spherical, or may be partially spherical, although it is believed that spherical geometry for particulate such as particles 127 is preferred. Furthermore, a partially spherical surface may be provided on the outside and/or the inside of particles 127, as for example a particle with a hollow spherical space therein. Particles 127 are made up of a different material than matrix 125. It is believed that the spherical shape provides for sound reflections at a variety of angles regardless of the direction from which the ultrasonic sound waves are emanating from, and accordingly, are more likely to reflect at least a portion of the transmitted signal back to the ultrasonic receiver to generate an image. Since many of the matrix materials available are relatively ultrasonically transparent in a patient, sound reflective particles 127 provide adequate reflection. The use of a composite, rather than a solution, provides adequate size for acoustic reflection off of the discrete particles embedded in the matrix. As indicated, a variety of materials may be utilized for the sound reflective particles, such as aluminum, hard plastic, sand, metal particles, and the like. Additionally, liquids, gases, gels, microencapsulants, and/or coacervates suspended in the matrix may alternatively be used either alone or in combination, so long as they form a composite with ultrasonically reflective particles in the matrix. Of this variety, glass balls have been found to be very well suited. For example, one commercially available supply of glass microspheres used for particle blasting is offered by Potters Industry, 377 Route 17, Hasbrouck Heights, N.J., U.S.A.

Another application is to have the matrix 125 compromise solder used to fuse parts together. For example, the solder matrix with sound reflective particles therein may be used to solder wires together in medical baskets (not shown) used to remove stones and other objects from medical patients. In addition to removal baskets, this technique may be used for other devices such as blood clot filters, guide wires and the like.

Figure 9A:
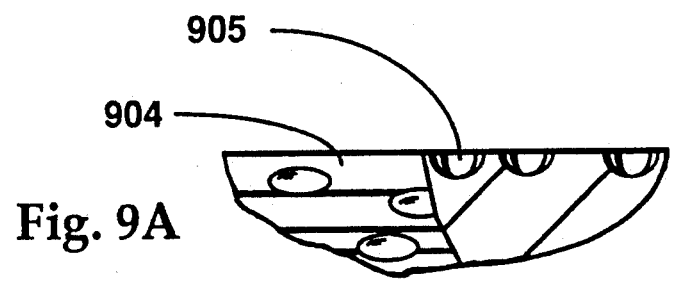
FIG. 9A is an enlarged portion of the medical device of FIG. 9.
Figure 9:
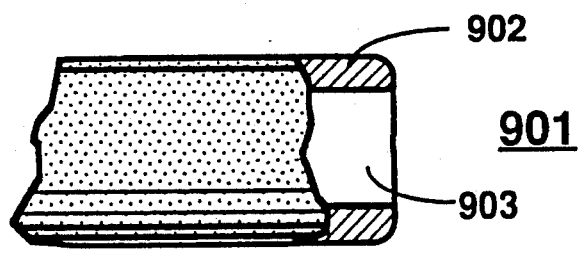
FIG. 9 is a partial cross-sectional view of another illustrative embodiment of the medical device of the present invention.

Depicted in FIG. 9 is a partial cross-sectional view of another illustrative embodiment of an echogenic medical device 901 that is insertable into a medium such as biological tissue or a passageway of a patient and that is sonically imageable with well-known sonic imaging equipment. As shown, medical device 901 comprises an elongated tubular member 902 with a passageway 903, commonly known as a lumen, extending longitudinally therein. Member 902 is part of any well-known catheter, stent, needle, and the like for insertion into a surrounding medium such as the biological tissue or passageway of a patient. The elongated member comprises a material having a first characteristic impedance, also referred to as acoustic impedance, different from the characteristic or acoustic impedance of the surrounding medium. Approximate values of characteristic or acoustic impedances for a variety of materials, both nonbiological and biological are disclosed in Table 1.4 of Wells, *Physical Principles of Ultrasonic Diagnosis*, Academic Press, London, New York, 1969, p. 10, and in Table 3.1 of McDicken, *Diagnostic Ultrasonics: Principle and Use of Instruments*, John Wiley & Sons, New York, 1976, p. 43. A mean characteristic impedance value for human tissue is indicated as $1.63 \times 10^6$ MKS rayl. Another table of characteristic impedances of various solids, liquids, and gasses are listed in Kinsler et al., *Fundamentals of Acoustics*, 2nd Edition, John Wiley & Sons, Inc., New York, 1962, pp. 502–503. The difference between the characteristic impedance of the member material and the surrounding medium enhances the intensity of an image produced in response to a sonic beam emitted from sonic imaging equipment. The magnitude of the difference is proportional to the enhancement factor. A more detailed discussion is found in Chapter III of the McDicken reference.

In one embodiment of medical device 901, elongated member 902 comprises a plastic material. From the Kinsler and Wells references, soft plastic such as polythene is listed as having a characteristic impedance of $1.84 \times 10^6$ MKS rayl. A hard plastic such as Lucite in bulk form is listed as having a characteristic impedance of $3.2 \times 10^6$ MKS rayl. When device 902 is inserted into the tissue or passageway of a patient, the difference in impedance between the tissue of the patient and the plastic material of the device is sufficient to enhance an image produced in response to a sonic beam from imaging equipment. As depicted in FIG. 9A, medical device 901 also includes an interface including outside surface 904 having a shape responsive to a sonic beam for producing one component such as a reflective component of the sonic image. The outside surface of the elongated member also includes a plurality of partially spherical indentations 905 therein. These partially spherical indentations scatter the sonic beam to produce another component of the image. A dimension of 2.5 microns is one acceptable size for the radius of partially spherical indentations 905. The radius of the indentations may range, for example, between 0.5 and 25 microns and beyond. This radial dimension is related to the wavelength of the incoming sonic beam in a predetermined manner such that the radius is much less than the wavelength of the beam. For example, a sonic beam emitted at 3.5 MHz has a wavelength of approximately 17,700 microns, whereas a sonic beam emitted at 7.5 MHz has a wavelength of approximately 8,200 microns. Both of these frequencies are emitted from commercially available ultrasonic imaging equipment.

The partially spherical indentations provide a curved surface from which the incident sonic beam may be scattered to produce the desired image regardless of the angle of incidence with respect to outer surface 904.

The image produced by the interface including the outer surface and partially spherical indentations includes one or more components. When the dimensions of an object such as the partially spherical indentations are very much less than the wavelength of the sonic beam, Rayleigh scattering occurs. One known example of Rayleigh scattering is the interaction of ultrasound with blood cells. As discussed in Chapter III of the McDicken reference, the intensity of the scattered wave depends on the acoustic impedance change at the interface, the dimensions of the interface and the wavelength of the sonic beam. The amplitude of the scattered wave component is proportional to the square of the frequency of the sonic beam. Therefore, high frequency sonic beams are scattered the most strongly. For a reflection component to occur, dimensions of the reflecting surface must be greater than several wavelengths of the incident sonic beam. A refraction component is also produced when the incident beam propagates through the interface with a change in direction governed by well-known Snell's law.

Depicted in FIG. 12 is a partial view of medical 1201 which is one embodiment of the present invention. The needle has partially spherical indentations 1202 in outer surface 1203 of tubular stainless steel cannula 1209. The indentations are grouped together in three millimeter bands 1204–1205 spaced approximately two millimeters apart about the distal end 1207 of the needle. A commercially available connector 1208 is positioned at the proximal end of the needle.

Depicted in FIG. 13 is a partial view of medical catheter 1301 which is another embodiment of the present invention. As depicted in FIG. 13A, this catheter embodiment also has partially spherical indentations such as 1302 in outer surface 1303 of flexible plastic material cannula 1304. This is just another example of the use of partially spherical indentations formed in the outer surface of an elongated member of a medical device as described with respect to FIGS. 9 and 9A. To ultrasonically image the catheter, three millimeter bands 1305–1309 of the indentations are grouped together and spaced approximately two millimeters apart about distal end 1310. As depicted in FIG. 13A, the exploded view of band 1308 and cross-sectional cannula 1304 more clearly exhibits partially spherical indentations 1302 in outer surface 1303. A commercially available connector 1311 is attached to the proximal end of the catheter.

The interface as depicted in FIG. 1 includes the generally spherical surface produced by the generally spherical particles 127 and matrix material 125. In such example, the generally spherical particles comprise glass, which has a characteristic or acoustic impedance ranging from 12.0 to $12.9 \times 10^6$ MKS rayls as indicated by the Kinsler reference. The acoustic impedance difference between the plastic matrix material 125 and the glass particles 127 is much greater than that of the plastic and tissue, thereby enhancing the scattered component of the image produced by the spherical surfaces. The surrounding medium includes the matrix material.

From another aspect, the matrix material is considered the member material having a first acoustic impedance, whereas the glass particles are considered a substance having a predetermined contour for establishing the interface. The particles are included within the member material and either embedded in or attached to the surface of the elongated member of the device. The interface surface forms one example of a particulate-type, discontinuous curved surface with discrete, particulate-type, discontinuous, acoustic discontinuities having a curved surface. In such case, the glass particles have a third acoustic impedance different from the acoustic impedance of the matrix material and surrounding biological tissue when inserted therein.

In another embodiment of medical device 905, elongated tubular member 902 comprises a stainless steel material having an acoustic or characteristic impedance in the range of 39.0 to $51.5 \times 10^6$ MKS rayls. Again, the outer surface of the elongated member includes a plurality of partially spherical indentations 905. Since the acoustic impedance difference between the stainless steel material and the surrounding tissue is even greater than that of glass or plastic and tissue, the intensity of the scattered component of the image produced from the partially spherical indentations is further increased.

The method of manufacturing medical device 901 includes forming the elongated member of the device from a material such as stainless steel or plastic as previously discussed, which has an acoustic impedance different from the biological tissue or medium in which the member is to be inserted. The interface is produced in one of several different manners. First, the elongated member may be extruded from one material and the partially spherical indentations formed or embossed in the material as the elongated member is being, for example, extruded. This would include the use of a well-known roller dye for selectively engaging the extruded material at designated positions. The dye would include at least partially spherical projections having the desired predetermined radius to form the indentations in the extruded material.

Figure 10A:
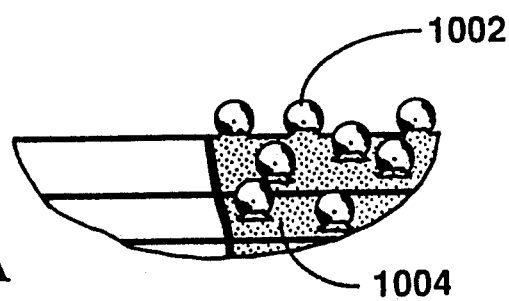
FIG. 10A is an enlarged portion of the medical device of FIG. 10.
Figure 10:
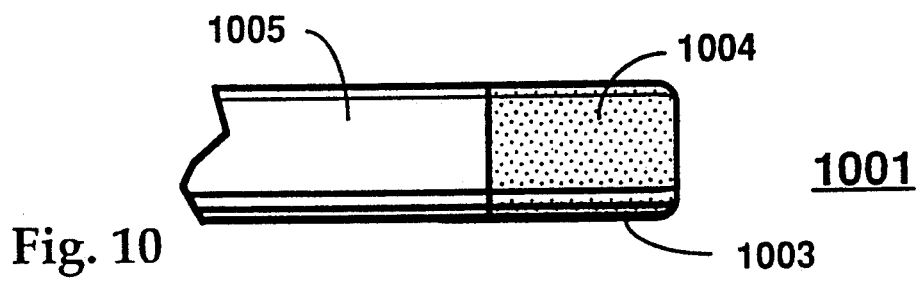
FIG. 10 is a partial view of still another illustrative embodiment of the medical device of the present invention.

Depicted in FIG. 10 is a partial view of another illustrative embodiment of medical device 1001. As depicted in FIG. 10A, a plurality of generally spherical particles 1002 consisting of, for example, lass may be attached to elongated tubular member 1003 using, for example, a well-known adhesive 1004. In such example, the elongated tubular member comprises any one of a plurality of well-known plastics having a flexibility or stiffness required for insertion into the tissue or passageway of the patient. In another embodiment of medical device 1001 of FIG. 10, spherical glass particles 1002 may be attached to a stainless steel tubular member using, for example, well-known silver solder. In such instance, the acoustic impedance of the glass particles as well as the silver solder may be considered in enhancing the produced image from an incident sonic beam.

Depicted in FIG. 14 is a partial view of medical stent 1401 having curled ends 1402 and 1403 for positioning the stent in a body passageway such as the ureter. The elongated plastic tubular member 1404 of the stent includes a plurality of ports 1405 for passing fluid therethrough. Similar to the configuration described with respect to FIGS. 10 and 10A, several bands 1406 of glass particles 1407 are attached to surface 1408 of the tubular member using a well-known medical grade adhesive 1409, as depicted in FIG. 14A. Alternatively, the glass particles are embedded in a matrix material that forms the plastic tubular member. The bands are approximately three millimeters in width and positioned approximately two millimeters apart at ends 1402 and 1403. The bands of glass particles may also be spaced along the entire length of the tubular member. The glass particles form an interface that is imageable with sonic imaging equipment. To provide a smooth outer surface for inserting the stent, a layer of plastic material 1410 coats the particles and surface 1408.

Figure 11A:
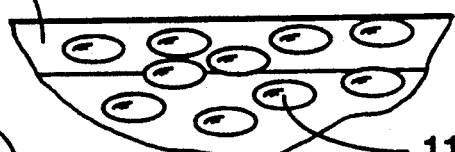
FIG. 11A is an enlarged portion of the medical device of FIG. 11.
Figure 11:
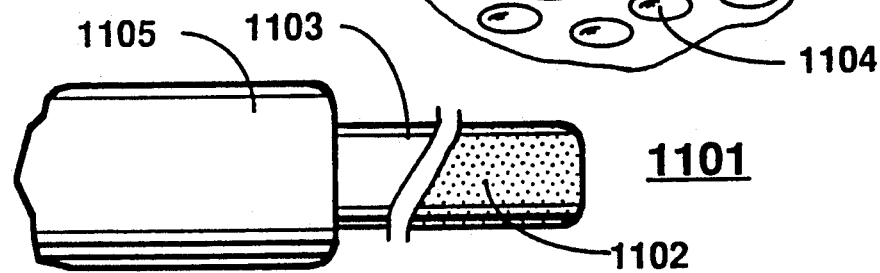
FIG. 11 is a partial view of the distal end of yet another illustrative embodiment of the medical device of the present invention.

Depicted in FIG. 11 is another illustrative embodiment of an echogenic medical device 1101 for insertion into biological tissue and imageable with sonic imaging equipment. Medical device 1101 comprises an elongated member such as cylindrical rod or stylet wire 1102 that is inserted into a passageway or lumen of catheter 1005 for inserting and guiding the catheter into a passageway or blood vessel of a patient. As depicted in FIG. 11A, the outside surface 1103 of the rod includes a plurality of partially spherical indentations 1104 for producing an image in response to a sonic beam from imaging equipment. Elongated member includes a material such as stainless steel with an acoustic impedance for enhancing any image produced by the partially spherical indentations in surface 1103. The elongated rod may be inserted into the lumen or passageway of a smooth outer surface catheter and inserted into a vessel of the patient and guided through the vessel with the assistance of the image produced by the indentations of the rod. The image produced by the indentations assists the physician in guiding the catheter and elongated rod through the passageway of the patient. This methodology includes directing a sonic beam toward the passageway of the patient with the device inserted therein and receiving an image from the indentations of the rod. Again, the material of the rod is selected to have an acoustic impedance different from that of the surrounding medium. It is envisioned that this surrounding medium may include body fluids from the patient or air which has an acoustic impedance of approximately 428 MKS rayls.

Figure 15:
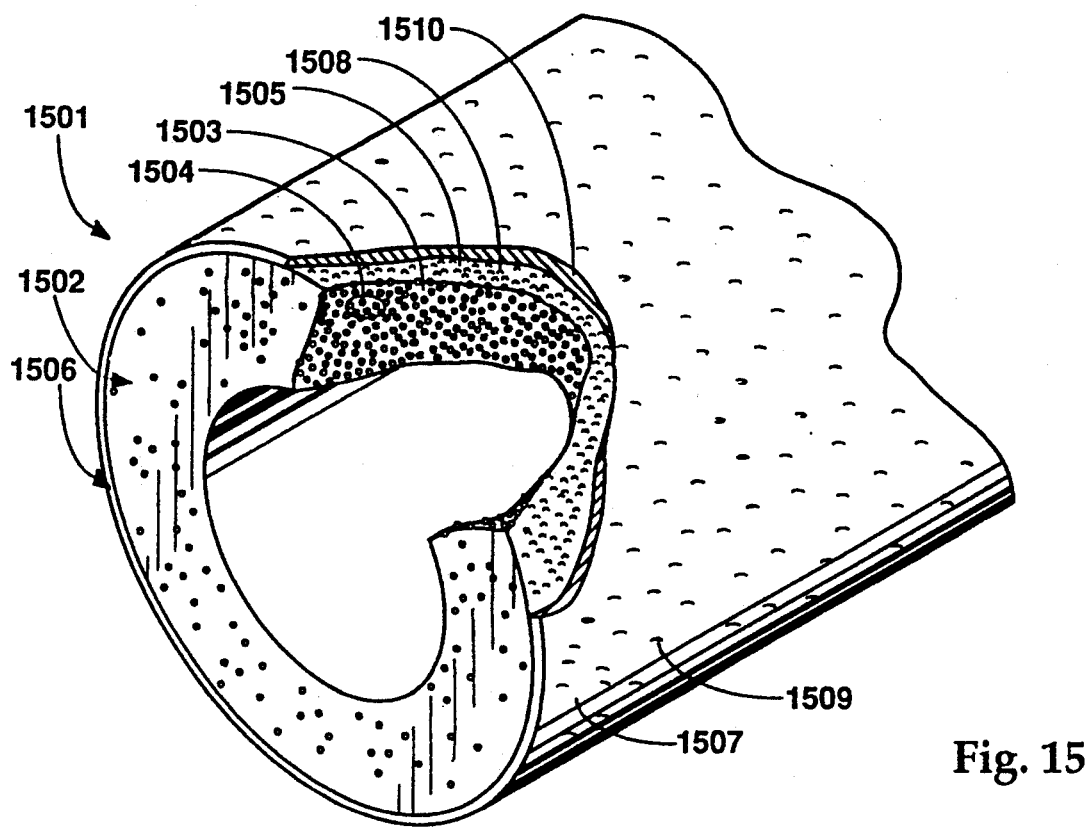
FIG. 15 is a partially sectioned view of a member of an alternative embodiment of the present invention with a high density interface layer deposited thereon.

Depicted in FIG. 15 is a partially sectioned view of flexible member 1501 of an alternative echogenic medical device having a high density metal interface layer 1506 deposited thereon for significantly enhancing the image of the device when inserted into a medium such as tissue or a passageway of a patient. The member comprises an elongated tube 1502 having a base or matrix material 1503 with particulate 1504 completely embedded therein. The elongated tube has an outer deposition surface 1505 of which particulate 1508 are at least partially embedded therein and at least partially extend therefrom. As a result, deposition surface 1505 forms a particulate type discontinuous curved surface with particulate 1508 forming discrete, particulate-type, discontinuous, acoustic discontinuities having a curved surface. A very thin interface layer 1506 of a high density metal 1510, approximately 2,000 to 3,200 angstroms in thickness, is deposited on deposition surface 1505 using ion beam assistance. The deposited interface layer conforms to deposition surface 1505 and has a similar outer, particulate-type, discontinuous curved surface 1507 as a result of particulate 1508 embedded in the deposition surface of the base material. The particulate have a dimension such as a 50 micron diameter preferably in the range of 1 to 100 microns, which is less than the wavelength of the sonic beam from the imaging equipment. The deposited interface layer covers surface particulate 1508 embedded in deposition surface 1505 of the base material to form discrete, particulate-type, discontinuous, curved surfaces 1509 in the outer surface of the interface layer.

The interface layer includes a high density metal material 1510 different from the flexible base material and has an acoustic impedance significantly different from the acoustic impedance of the medium of which the device is inserted therein. When the device is exposed to a sonic beam from the imaging equipment, the increased difference between the acoustic impedances of the interface layer material and the surrounding medium significantly enhances the image of the member in the medium.

Base material 1503 of the elongated tube preferably comprises a commercially available, medical grade polyurethane, which is suitable for placement in the urinary system of a patient. As previously suggested, the medical device can take the form of a catheter or stent which is insertable into the urethra, bladder, ureter, or kidney of the patient. This polyurethane material is sufficiently flexible for atraumatic insertion through these portions of the urinary system, but is sufficiently pushable for placement. Alternatively, base material 1503 is a material selected from a group consisting of silicone, polyethylene, nylon, C-FLEX TM, polytetrafluoroethylene, polyvinyl chloride, polypropylene, polyester, and other medical grade polymers. C-FLEX TM material is a styrene-ethylene-butylene-styrene block copolymer plasticized with various proportions of silicone and mineral oils and is commercially available from Concepts Polymer Technologies, Inc. of Clearwater, Fla. In addition to experiments performed with polyurethane, it was observed that the adherence of 2800 angstrom interface layer of titanium to the deposition surface of polyethylene and nylon was found not to be as good as that of the polyurethane. The acoustic impedance of these base materials are disclosed in the previously described references or are available from the manufacturers thereof. The acoustic impedance of these materials are sufficient to establish a difference between that of the surrounding medium to produce and enhance an image of the member in response to a beam from sonic imaging equipment. However, to further enhance the acoustic impedance difference particulate are mixed with the base material during the formation of the tube. Particulate 1504 and 1508 include a plurality of particles such as tungsten spheres having a diameter of approximately 50 microns. These 50 micron tungsten spheres are commercially available from the GTE Company of Towanda, Pa. The density of the tungsten spheres is approximately 19.3 grams per cubic centimeter. The volume of the tungsten spheres to that of the polyurethane material is approximately 30 percent. Alternatively, the particles comprise glass material spheres also having a diameter of approximately 50 microns. Experimentally, the glass spheres produced images in less dense tissue such as that of the uterus and bladder. The high density metal tungsten spheres produced better images in this less dense tissue and in higher density tissue such as the ureter and kidney. The glass beads did not produce the same quality images as that of the tungsten spheres in the higher density tissue.

Figure 16:
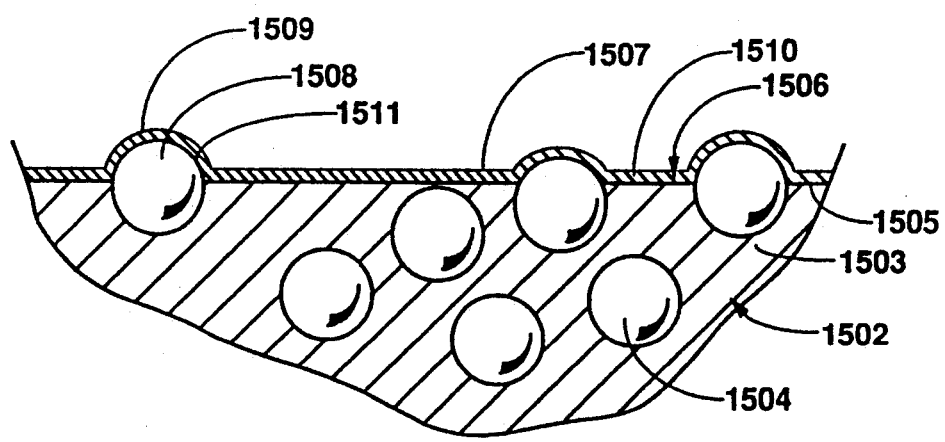
FIG. 16 is an enlarged view of a section of the interface layer and the base material of the member of FIG. 15.

Depicted in FIG. 16 is an enlarged view of base material 1503 with particulate 1504 completely embedded therein and particulate 1508 at least partially embedded in and extending from deposition surface 1505. Surface particulate 1508 form discrete, particulate-type, discontinuous curved surfaces 1511 in deposition surface 1505. For nonflexible medical device applications, the base material comprises a rigid material such as stainless steel or other rigid metal or polymer materials. It is also contemplated that the spheres are attached to the base material as described with respect to FIGS. 10A and 14A.

Interface layer 1506 of high density metal material 1510 is deposited on surface particulate 1508 and deposition surface 1505 of the base material. The deposition of high density material 1510 is ion beam assisted. Ion beam assisted deposition of the high density material is commercially available from the Spire Corporation of Bedford, Mass. The high density deposition material has a higher acoustic impedance than that of base material 1503 to further increase the acoustic impedance difference between that of the surrounding medium. The high density material preferably comprises titanium which is deposited as a layer having a thickness in a range of approximately 2,000 to 3,200 angstroms. This ion beam assisted deposition of the high density material readily adheres to the deposition surface of the base material while maintaining the overall flexibility of the base material. This ion beam assisted deposition process is conducted in a vacuum chamber to bombard the deposition surface of the polyurethane base material with argon ions and to produce a smooth, nonporous polyurethane surface for vacuum deposition of the titanium thereon. Bombarding ions are selected as a function of the base material. Alternatively, the deposition material of the interface layer includes a metal from the group consisting of tungsten, platinum, silver, gold, palladium, barium, and bismuth.

Interface layer material 1510 deposited on surface particulate 1508 forms the discrete, particulate-type, discontinuous curved surfaces 1509. The extremely thin interface layer permits the partially curved surface of the embedded particulate to be represented on the outer surface of the interface layer. These discontinuous curved surfaces in combination with the acoustic impedance difference established between the interface layer and the surrounding medium cooperate to significantly enhance the ultrasonic image of the medical device when inserted in the medium.

Figure 17:
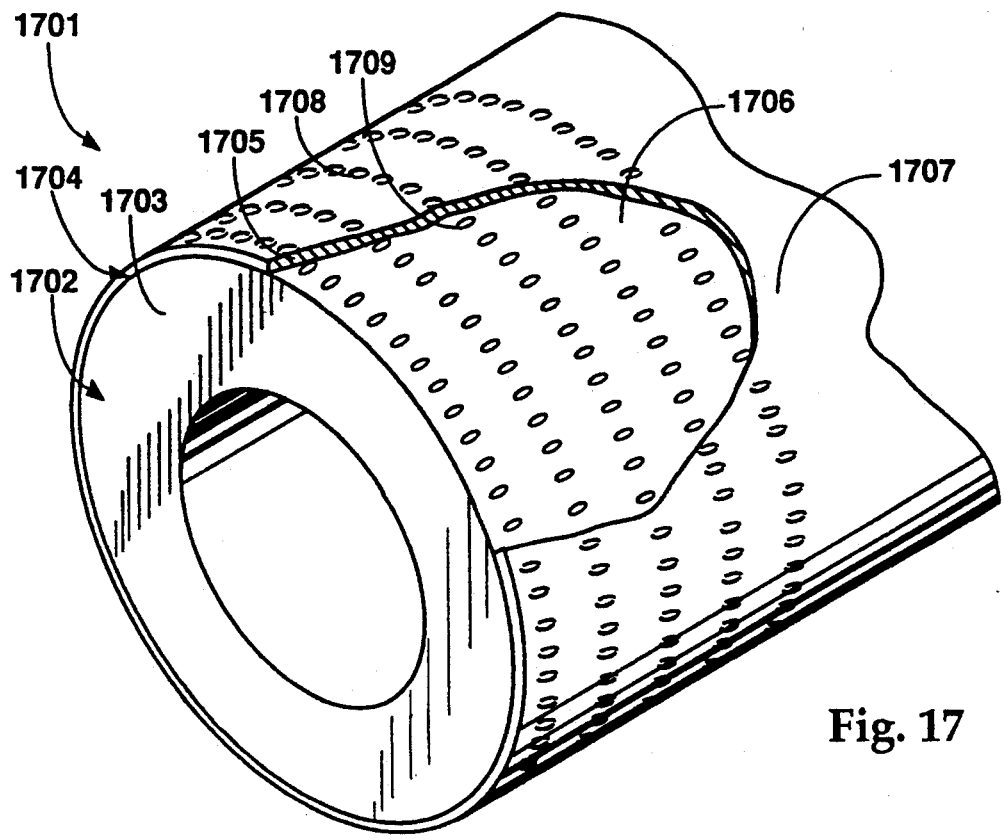
FIG. 17 is a partially sectioned view of a member of an alternative embodiment of the present invention as depicted in FIG. 15 with at least partially spherical indentations formed in the surface thereof.

Depicted in FIG. 17 is a partially sectioned view of member 1701 which is an alternative embodiment of member 1501 of FIG. 15. Member 1701 comprises an elongated tube 1702 having base material 1703 as previously described. Member 1703 also includes an interface layer 1704 of high density material 1705, as also previously described, deposited on deposition surface 1706 of elongated tube 1702. The interface layer includes an outer surface 1707 of which discrete, particular-type, discontinuous curved surfaces 1708 are formed therein. Curved surfaces 1708 comprise a plurality of at least partially spherical indentations which conform to the at least partially spherical indentations 1709 formed in base material 1703. Indentations 1709 are formed in deposition surface 1706 of the base material in a uniform manner with a radius in the range from 0.5 to 50 microns.

Figure 18:
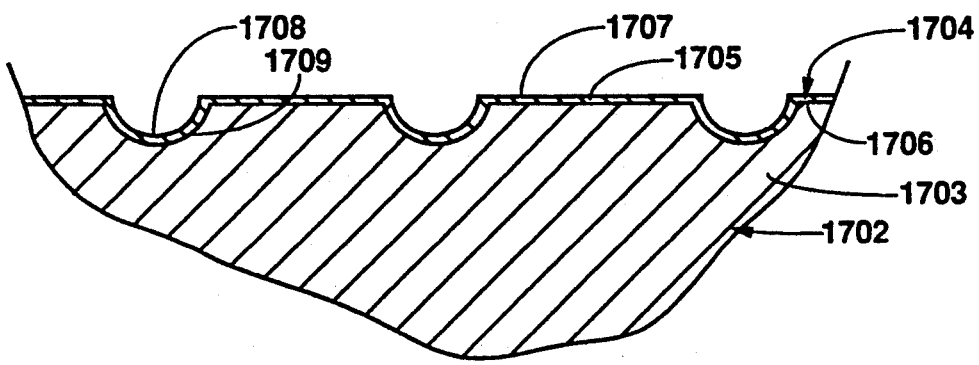
FIG. 18 is an enlarged view of a section of the interface layer and the base material of the member of FIG. 17.

An enlarged view of indentations 1709 formed in deposition surface 1706 of the base material 1703 is depicted in FIG. 18. Interface layer 1704 of high density material 1705 is deposited on surface 1706 of the base material as previously described using ion beam assistance. Indentations 1709 are formed approximately 0.005" apart in the deposition surface of the base material in a uniform array as shown. The thickness of interface layer 1704 is also preferably in a range of approximately 2,000 to 3,200 angstroms. Although the thickness of the interface layer is preferably in a range from 2,000 to 3,200 angstroms, the thickness may vary as a result of the base material and high density interface material selected. Although the interface layer has been described as preferably comprising one layer of deposited metal, two or more layers of similar or dissimilar materials are also contemplated for deposition.

FIG. 2 discloses a second embodiment of the present invention setting forth one of many shapes or embodiments the present invention may include, in this case a catheter. Echogenic body member 223 forms a catheter with catheter wall 231 surrounding lumen 229. Lumen 229 has an inside diameter ID. In one embodiment, this internal diameter may be 0.040 inches. The outside diameter OD of iiii body member 223 in this particular embodiment is 0.065 inches. The outside diameter X of one of the typical, illustrated microspheres in this particular embodiment is 5 microns, or 5 one-millionths of a meter. A typical reflective particle, sound reflective particle 227, is illustrated embedded in matrix material 225 similar to that previously described.

Referring to FIG. 3, a third embodiment is shown with iiii body member 323 being a two lumen catheter with lumen 329a and lumen 329b being disposed in catheter wall 331. A multitude of sound reflective particles are illustrated, such as sound reflective particle 327 embedded in matrix material 325.

Referring to FIG. 4, a fourth embodiment is illustrated as echogenic body member 423 which is a triple lumen catheter having lumen 429a, lumen 429b, and lumen 429c within catheter wall 431. Sound reflective particles, such as sound reflective particle 427 are shown in matrix 425.

Referring to FIG. 7, a fifth embodiment is shown with catheter wall 731 supporting echogenic body member 723. Member 723 is a composite as described above, with the matrix material being a painted on adhesive with sound reflective particles, such as particle 727, therein. Lumen 729 is in catheter wall 731. The sound reflective body is painted onto only a portion of the catheter as an annular stripe which is to be imaged.

Referring to FIG. 8, echogenic body member 823 is in the form of a fishing lure, such as a plastic nightcrawler with metal hook 853 and sinker 855 popular with fisherman. Matrix material 825 is the plastic body of the worm with sound reflective particles, such as particle 827, therein. This is one of the many applications. Fisherman using a sonar type depth finder/fish finder may have enhanced imaging of lure 823 using the present invention.

As indicated, the foregoing embodiments are merely representative, and the present invention is not only restricted to medical devices. However, the benefits of the present invention are especially well suited for medical devices such as catheters.

The proportions between matrix material and the sound reflective particles may be measured by their percentage volume of the composite material. Typically, the composite material made up of between about 5% and 30% of the sound reflective particles by volume. One preferred embodiment has the composite material made up of about 10% of the sound reflective particles by volume. Another embodiment has about two to three percent sound reflective particles by volume. However, one percent or even a fraction of one percent, and up to 60% by volume of the sound reflective particles have been tested and determined to be acceptable for at least some applications. Nevertheless, as the percentage volume of the sound reflective particles increase, the amount of matrix material cohesively bonding the particles together is reduced. Accordingly, there ultimately occur trade-offs in terms of flexibility, durability, and cohesiveness. Furthermore, even ranges of less than 5% volume of sound reflective particles may be utilized in specific applications. Certain medical instruments such as an iiii ruler may utilize the composite material of the present invention only in selected localized positions on the medical device. Such selected localization may include the use of only one, or only a few, sound reflective particles. The matrix material may be a glue or other compound which can be painted or otherwise applied to localized regions on the device where only that region of the device needs to be imaged echogenically (see e.g. FIG. 7). It is noteworthy that in at least certain applications, such as catheters, where the sound reflective particles comprise about 30% of the volume of the composite material, no significant loss in tensile strength was detected.

Figure 5:
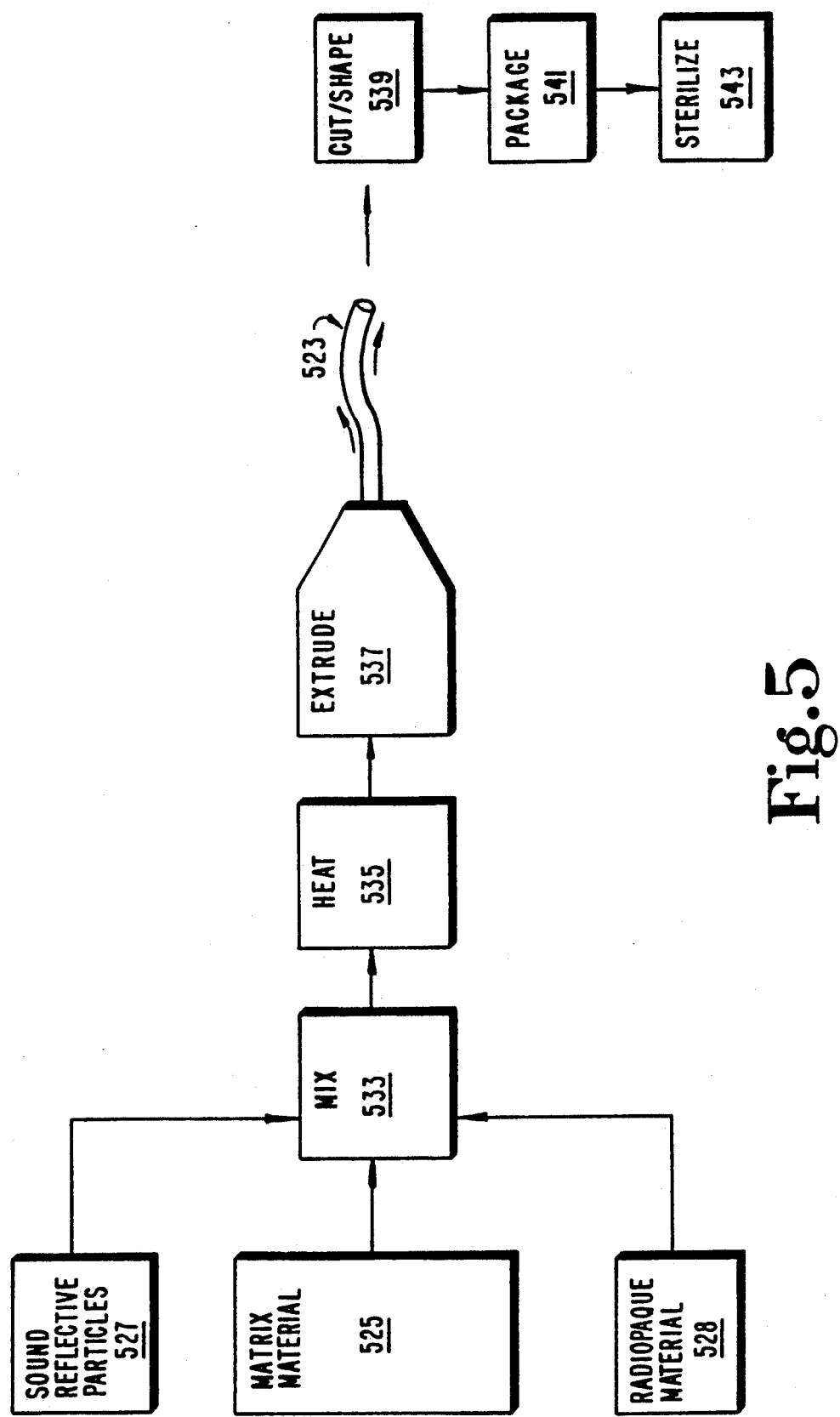
FIG. 5 is a schematic diagram of a method of fabrication according to the present invention.

Referring to FIG. 5, a schematic diagram of at least one method of fabricating the present invention is illustrated. Matrix material 525 may comprise plastic pellets which may be mixed with sound reflective particles 527 in the mixing step 533. Mixing may occur by gravity feed of the parts to be mixed into a screw or worm-gear type mechanism well known in extruder machines such as are used for catheter manufacture. Optionally, but not necessarily, radiopaque material 528 may also be mixed with the matrix material and the sound reflective particles. The radiopaque material may be one of numerous radiopaque materials already known, as for example, barium, bismuth or tungsten. The radiopacifier may be finely ground powder mixed during the mixing step 533. Before, during or after the mixing step 533 the mixture may be heated in the heating step 535. The heating maintains the matrix material in a molten or liquid state allowing it to be formed to the desired shape. During the forming step 537, which is illustrated as an extruding step known in the catheter industry, the composite mixture is formed into an iiii body member 523, including the sound reflective particles from 527 embedded in the matrix material. As illustrated, iiii body 523 is a tubular catheter body having a longitudinal lumen as previously described. Other types of forming may be used, such as molding or other such shaping. Thereafter, the iiii body member may be cut and/or shaped, as for example, cut into a specified length and/or cutting side drainage lumens, curling, tapering, or other such processes known in the plastics industry and in the catheter industry. Thereafter, the medical device is packaged during the packaging step 541, preferably hermedically sealed as is known to maintain the medical device in a surgically sterile condition. Finally, the medical device may be sterilized during the sterilizing step 543, using heat, chemicals, or other known techniques.

Figure 6:
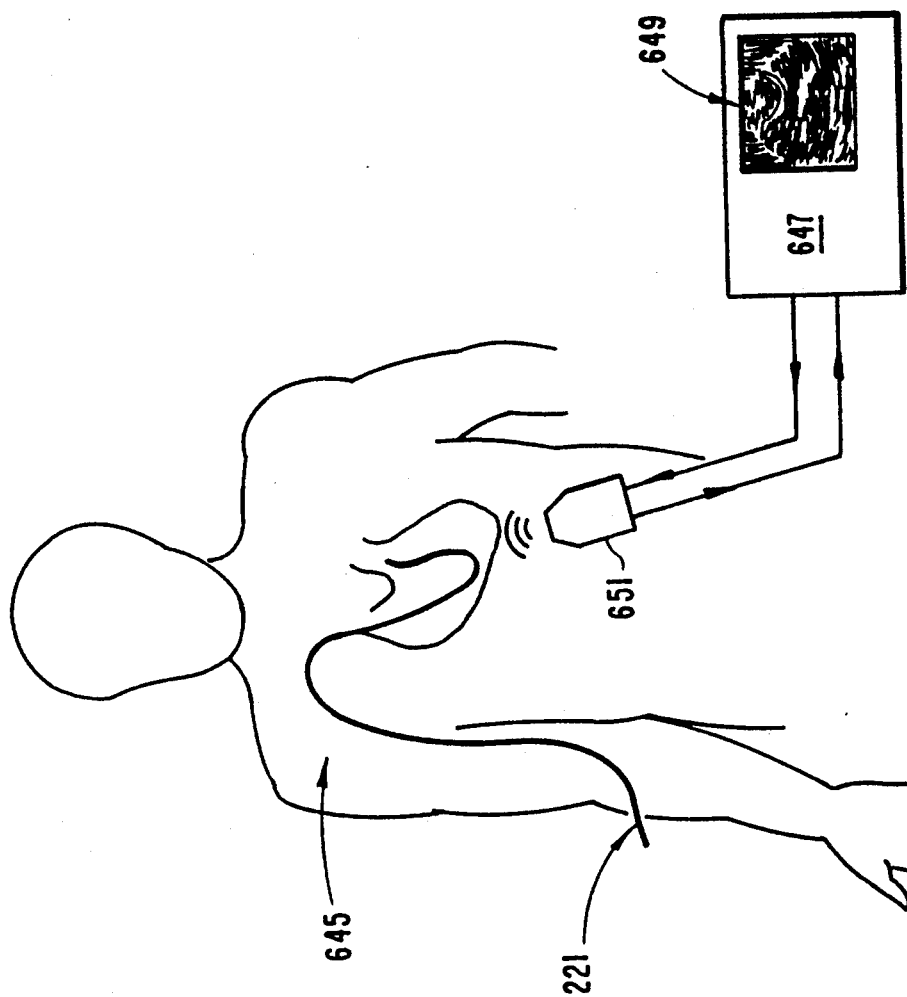
FIG. 6 illustrates one embodiment of the present invention inserted in a medical patient.

FIG. 6 shows an iiii medical device 221 according to the present invention inserted surgically into medical patient 645. As illustrated in FIG. 6, a tubular catheter is utilized, it being understood that this is only one of many devices according to the present invention. Device 221 is sonically imaged using imaging device 647 with probe 651 to create image 649. This method of use involves placing a device according to the present invention in the sonic imaging beam or field of the probe as illustrated and using equipment, such as well known ultrasonic imaging equipment, to produce image 649.

Figure 19:
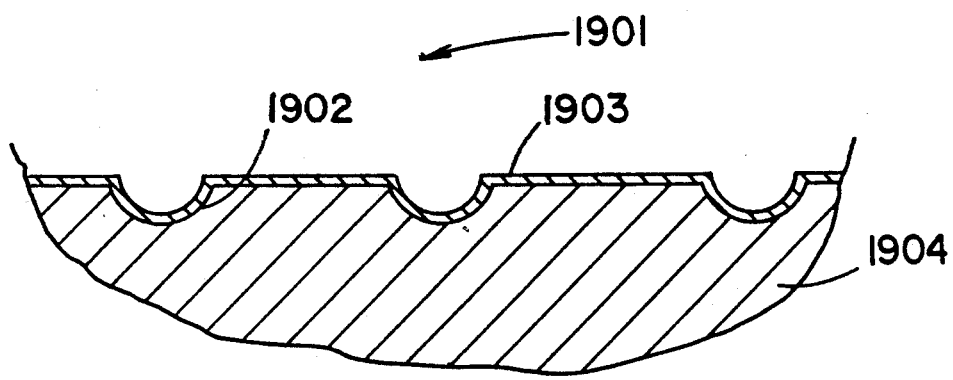
FIG. 19 is an enlarged view of the indentations in the outer surface of a base material of an alternative embodiment of the elongated member of FIG. 15.

Depicted in FIG. 19 is an enlarged view of indentations 1902 formed in outer surface 1903 of first base material 1904 of elongated member 1901, which is an alternative embodiment of member 1501 of FIG. 15. Member 1901 comprises an elongated tube having first base material 1904, as previously described. Member 1901 also includes outer surface 1903 which has been bombarded in a vacuum chamber environment with argon ions.

In this embodiment, first base material 1904 comprises a polyurethane which when untreated exhibits a first coefficient of friction of approximately 0.449. Outer surface 1903 has been bombarded with ion beams and exhibits a second coefficient of friction of approximately 0.124. However, the elongated member material may comprise any material from a group consisting of polyurethane, polythylene, nylon, C-FLEX TM, polytetrafluoroethylene, polyvinyl chloride, polypropylene, and polyester. Alternatively, elongated member 1901 comprises a silicone 30 rubber material having a durometer in the range of 30–80 on the Shore A scale. In this particular embodiment, the silicone rubber material has a durometer of 70 on the Shore A scale. This silicone rubber material is a commercially available medical grade silicone rubber which has been treated by bombarding outer surface 1903 with ions such as argon in a vacuum chamber environment. This ion beam bombardment or implantation is commercially available from such companies as the Spire Corporation, Bedford, Mass. The catheter is initially formed with a first base material such as polyurethane or silicone rubber, which when untreated with argon ions exhibits a coefficient of friction of approximately 0.449 for untreated polyurethane and approximately 0.211 for untreated silicone rubber. The untreated base material catheters are placed in a vacuum chamber for argon ion beam bombardment. The untreated base material catheters are exposed to an ion argon beam while the catheter is rotated in the chamber to expose the entire outside surface of the catheter to the argon ion beam. When so treated, outer surface 1903 of the base material is implanted with argon ions to smooth the surface thereof. The coefficient of friction of treated outer surface 1903 is significantly reduced such as, for example, to approximately 0.124 for polyurethane and 0.125 for silicone rubber. A series of well-known fluid contact angle tests to determine the hydrophilic or hydrophobic character of the surface have indicated that a water contact angle of 75° to 95° results in a thromboresistant surface. This also results in a surface energy of 20 to 30 dynes per centimeter. This particular range of surface energy has been found to be resistant to the formation of blood thrombus on the surface of a device in contact with blood as disclosed by Dr. Baier in his "Selected Methods of Investigation for Blood-Contact Surfaces", *Annals of the New York Academy of Sciences*, vol. 516, Dec. 28, 1987, pp. 68-77. It is further believed that the probable effects of ion implantation on a base material of polyurethane or silicone rubber include material densification, redistribution of surface charges, reorientation of surface chains, and chain scission followed by chain cross-linking. It is further believed that the surface of the base material is carbon enriched. It is further believed that the outer surface of polyurethane or silicone rubber with the aforementioned range of surface energy is also resistant to the formation and growth of fungus, bacteria, and encrustations. Although the above description of the catheter with treated outer surface 1903 has been with respect to silicone rubber or polyurethane, any base material from the previously described group of materials with, for example, argon produces similar results. The ion used for bombardment of the outer surface varies as a function of the material selected. Other ions include the use of nitrogen, oxygen, neon, and the like for bombarding various polymer materials. Although described for use as a stent, catheter, cannulae, and the like, the outer surface treatment of any medical device intended for use in contact with any body fluid is contemplated.

Figure 20:
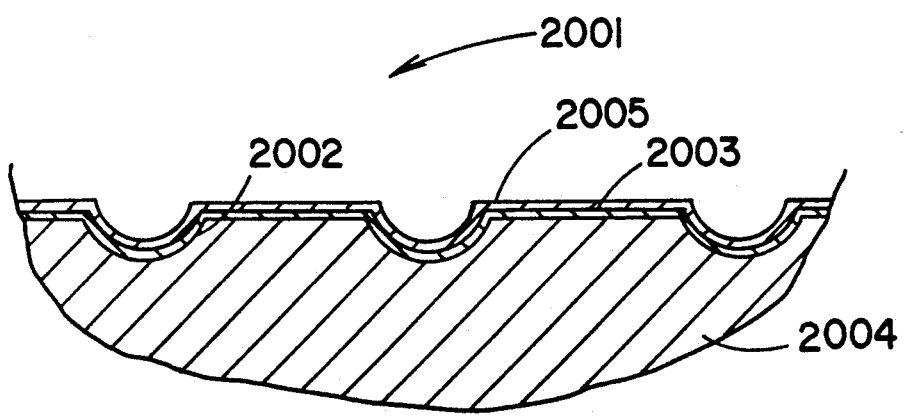
FIG. 20 is an enlarged view of the indentations in the outer surface of a base material of an alternative embodiment of the elongated member of FIG. 19 with an interface layer deposited thereon.

Depicted in FIG. 20 is an enlarged view of indentations 2002 formed in outer surface 2003 of first base material 2004 of elongated member 2001, which is an alternative embodiment of member 1901 of FIG. 19. In this embodiment, an interface layer 2005 has been deposited using ion beam assisted deposition as previously described. Member 2001 comprises an elongated tube having first base material 2004, as previously described. Member 2001 also includes outer surface 2003 which has been bombarded in a vacuum chamber environment with argon ions to reduce the coefficient of friction and to bring the surface energy of the outer surface within the range of 20 to 30 dynes per centimeter. Interface layer includes a metal from the group consisting of titanium, tungsten, barium, bismuth, silver, gold, platinum, and palladium, which are different from base material 2004, as previously described. In this embodiment with interface layer 2005 deposited on outer surface 2003, the coefficient of friction is approximately 0.184.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Although the particles have been described preferably a generally spherical or partially spherical in shape, the shape may include any geometric shape having one or more flat or curved surfaces having a dimension for producing a scattered component of the image. Naturally occurring crystalline structures are also contemplated.

What is claimed is:

1. A treated surface catheter, stent, or cannulae, comprising:
   an elongated member including a first predetermined material having a first surface energy; and
   an outer surface of said member including said first material and having a second surface energy different from said first surface energy and in a range of 20 to 30 dynes per centimeter.

2. The treated surface catheter, stent, or cannulae of claim 1 wherein said first material includes a base material from a group consisting of polyurethane, polyethylene, nylon, C-FLEX TM, polytetrafluoroethylene, polyvinyl chloride, polypropylene, polyester, and silicone.

3. The treated surface catheter, stent, or cannulae of claim 2 wherein aid elongated member is for insertion into a medium having a first acoustic impedance, said member including an interface layer on said first material, said interface layer having a particulate-type, discontinuous curved surface having a dimension less than a wavelength of a sonic beam from sonic imaging equipment, said interface layer including a second material different from said first material and having a second acoustic impedance different from said first acoustic impedance of said medium, said first and second acoustic impedance having at least a predetermined difference therebetween, whereby said difference between said first and second acoustic impedances and said curved surface cooperate in response to said sonic beam to produce an image of said member.

4. The treated surface catheter, stent, or cannulae of claim 3 wherein said first material exhibits a first coefficient of friction and wherein said outer surface exhibits a second coefficient of friction less than said first coefficient of friction.

5. The treated surface catheter, stent, or cannulae, of claim 4 wherein said interface layer has a surface energy in the range of 20 to 30 dynes per centimeter.

6. The treated surface catheter, stent, or cannulae of claim 1 wherein said first material includes polyurethane.

7. The treated surface catheter, stent, or cannulae of claim 6 wherein said outer surface of said first material has been ion beam bombarded with predetermined ions and, as a result, has said second surface energy.

8. The treated surface catheter, stent, or cannulae of claim 7 wherein said first material has a first coefficient of friction and said outer surface of said first material has a second coefficient of friction less than said first coefficient of friction.

9. A treated surface catheter, stent, or cannulae comprising:
   an elongated member including a first predetermined material having a first surface energy; and an outer surface including said first material and having a second surface energy different from said first surface energy, water when applied to said outer surface beading and forming a contact angle in a range of 75° to 95°.

10. The treated surface catheter, stent, or cannulae of claim 9 wherein said first material includes a base material from a group consisting of polyurethane, polyethylene, nylon, C-FLEX TM, polytetrafluoroethylene, polyvinyl chloride, polypropylene, polyester, and silicone.

11. The treated surface catheter, stent, or cannulae of claim 9 wherein said first material includes polyurethane.

12. The treated surface catheter, stent, or cannulae of claim 11 wherein said first material has been ion beam bombarded with predetermined ions and, as a result, has said second surface energy.

13. The treated surface catheter, stent, or cannulae of claim 9 wherein said first material exhibits a first coefficient of friction and said outer surface of said first material exhibits a second coefficient of friction less than said first coefficient of friction.

14. The treated surface catheter, stent, or cannulae of claim 9 wherein said first material includes a composite material echogenically imageable, said composite material including a solid matrix material and discrete sound reflective particles fixedly positioned throughout said matrix material ultrasonically different from tissue and more sonically reflective than said matrix material to enhance the echogenicity of said first material, said first material also including an outer layer ion beam deposited on said outer surface to further enhance the echogenicity of said elongated member.

15. An echogenic medical device insertable into a medium and imageable with sonic imaging equipment, comprising:
a member for insertion into a medium having a first acoustic impedance, said member including a base material from a group consisting of polyurethane, polyethylene, nylon, C-FLEX TM, polytetrafluoroethylene, polyvinyl chloride, polypropylene, polyester, and silicone and an interface layer deposited on said base material, said base material having an outer surface having a surface energy in a range of 20 to 30 dynes per centimeter, said interface layer deposited on said outer surface forming a deposition surface and having a discrete, particulate-type, discontinuous curved surface having a diameter less than a wavelength of a sonic beam from said imaging equipment, said member including a particulate in said deposition surface for forming said particulate-type, discontinuous surface in said deposition surface, said particulate including a plurality of particles from a group of tungsten and glass materials in a generally spherical shape, said interface layer including a metal from a group consisting of titanium, tungsten, barium, bismuth, silver, gold, platinum, and palladium different from said base material and having a second acoustic impedance different from said first acoustic impedance of said medium, said first and second acoustic impedances having at least a predetermined difference therebetween, said metal of said interface layer having been vacuum deposited on said deposition surface of said base material using ion beam assistance, whereby said difference between said first and second acoustic impedances and said curved surface responds to said sonic beam to produce an image of said member.

16. A medical device intended for use in contact with body fluid, said device comprising a member of a first predetermined material exhibiting a first coefficient of friction;
said member comprising an outer surface of said first material having been treated by ion beam bombardment with predetermined ions and exhibiting a second coefficient of friction less than said first coefficient of friction and wherein said outer surface of said first material has a surface energy within a range of 20 to 30 dynes per centimeter.

17. The medical device of claim 16 wherein said first material is from a group consisting of polyurethane, polyethylene, nylon, C-FLEX TM, polytetrafluoroethylene, polyvinyl chloride, polypropylene, polyester, and silicone.

18. The medical device of claim 17 wherein said first material has been treated by ion beam bombardment with argon ions.

19. The medical device of claim 16 wherein said outer surface has a surface energy and, when water is applied thereto, said outer surface forms a contact angle in a range of 75° to 95°.

* * * * *